United States Patent [19]

Tani

[11] Patent Number: 4,626,908
[45] Date of Patent: Dec. 2, 1986

[54] TRACKING INPUT DEVICE

[75] Inventor: Yuichiro Tani, Yaita, Japan

[73] Assignee: Tokyo Shibaura Denki Kabushiki Kaisha, Kawasaki, Japan

[21] Appl. No.: 554,236

[22] Filed: Nov. 22, 1983

[30] Foreign Application Priority Data

Nov. 22, 1982 [JP] Japan .................. 57-203592

[51] Int. Cl.[4] .......................... H05G 1/64; H04N 5/32
[52] U.S. Cl. .................................. 358/111; 358/125; 378/99
[58] Field of Search ............... 250/203 R; 378/62, 99, 378/100; 358/110, 111, 125; 382/6, 60

[56] References Cited

U.S. PATENT DOCUMENTS

| | | | |
|---|---|---|---|
| 3,419,674 | 12/1968 | Burns et al. | 358/125 |
| 3,444,380 | 5/1969 | Webb | 358/125 |
| 3,522,585 | 8/1970 | Lemay | 382/6 |
| 3,967,053 | 6/1976 | Grosskopf | 382/6 |
| 4,364,089 | 12/1982 | Woolfson | 358/125 |
| 4,409,615 | 10/1983 | McMann, Jr. et al. | 378/99 |

FOREIGN PATENT DOCUMENTS

| | | | |
|---|---|---|---|
| 2041530 | 8/1970 | Fed. Rep. of Germany | 358/125 |
| 2754687 | 6/1978 | Fed. Rep. of Germany | 358/125 |
| 0073180 | 6/1980 | Japan | 358/125 |
| 0147287 | 9/1983 | Japan | 358/111 |

Primary Examiner—Bruce C. Anderson
Assistant Examiner—Charles F. Wieland
Attorney, Agent, or Firm—Finnegan, Henderson, Farabow, Garrett & Dunner

[57] ABSTRACT

Disclosed is an image input device arranged in such a way that a fluorescent X-ray image is imaged by a TV camera, and an image signal thereof is input into a CPU. The image input device is connected to an output of the TV camera, and comprises a difference circuit for determining the difference between two picture signals obtained at a prescribed time interval, an object extracting circuit for extracting an object image in accordance with the results of the difference, a position judging circuit for judging whether or not the object image thus extracted is located within a picture screen, and a camera position controller for controlling the position of the TV camera in accordance with the results of judgement made by the position judging circuit.

5 Claims, 6 Drawing Figures

TRACKING INPUT DEVICE

BACKGROUND OF THE INVENTION

The present invention relates to an image input device used in inputting an image into an image processing apparatus.

With the recent progress in image processing techniques, various image processing methods have hitherto been employed in the medical field, as well. For example, angiography is used as one method of diagnosis of the circulatory organs. This method consists of inserting a catheter into the heart or blood vessels, injecting a contrast medium into the blood vessels through the catheter, and imaging the flow of the resultant contrast medium by an X-ray imaging apparatus. The X-ray image obtained through the irradiation of X-rays is imaged by a TV camera, and the output image signal from the TV camera is converted to a digital signal by an analog-to-digital converter. The digital signal is input into a computer, whereby the image processing is carried out.

When a portion to be diagnosed, which is injected with such a contract medium, is imaged, the position thereof on the entire picture screen, the magnification thereof, etc., are widely varied, according to the imaging conditions. Furthermore, since portions to be diagnosed might include such portions as, e.g., the heart, which change in shape over time, it is likely that the object to undergo diagnosis will be displaced from the central portion of the picture screen; or, at worst, will be partially or wholly lost from the screen.

In the prior art, therefore, image inputting has been carried out while the position and configuration of the object on the picture screen are being anticipated and the imaging condition is being adjusted accordingly. However, if a person making the image were to sensuously evaluate the position, configuration, and amount of variation over time of the object, and change the imaging condition accordingly, such an operation would be very time-consuming. In other words, as the number of images obtained was increased, the amount of time required would become exorbitant. Particularly when image processing is carried out on an on-line basis, a serious problem arises, in that the quantity of X-rays to be irradiated onto a patient increases.

SUMMARY OF THE INVENTION

In view of the above, the object of the present invention is to provide an image input device wherein the imaging conditions can be varied in accordance with the variation in position and configuration of the object to be diagnosed and an image thereof can be input while the object image is being kept located in the central portion of the picture screen.

The above object can be attained by an image input device comprising a imaging section for imaging a picture including an object to be diagnosed, which object varies in position and configuration over time, an object extracting circuit for extracting an object image by determining the difference in brightness between the two pictures obtained from the imaging section at a prescribed time interval, a position judging circuit for judging whether or not the extracted object is located within a predetermined portion of a picture screen, and a control circuit for controlling the imaging conditions of the imaging section in accordance with the results of judgement made by the position judging circuit.

DETAILED DESCRIPTION OF THE PREFERRED EMBODIMENT

Figure 1:
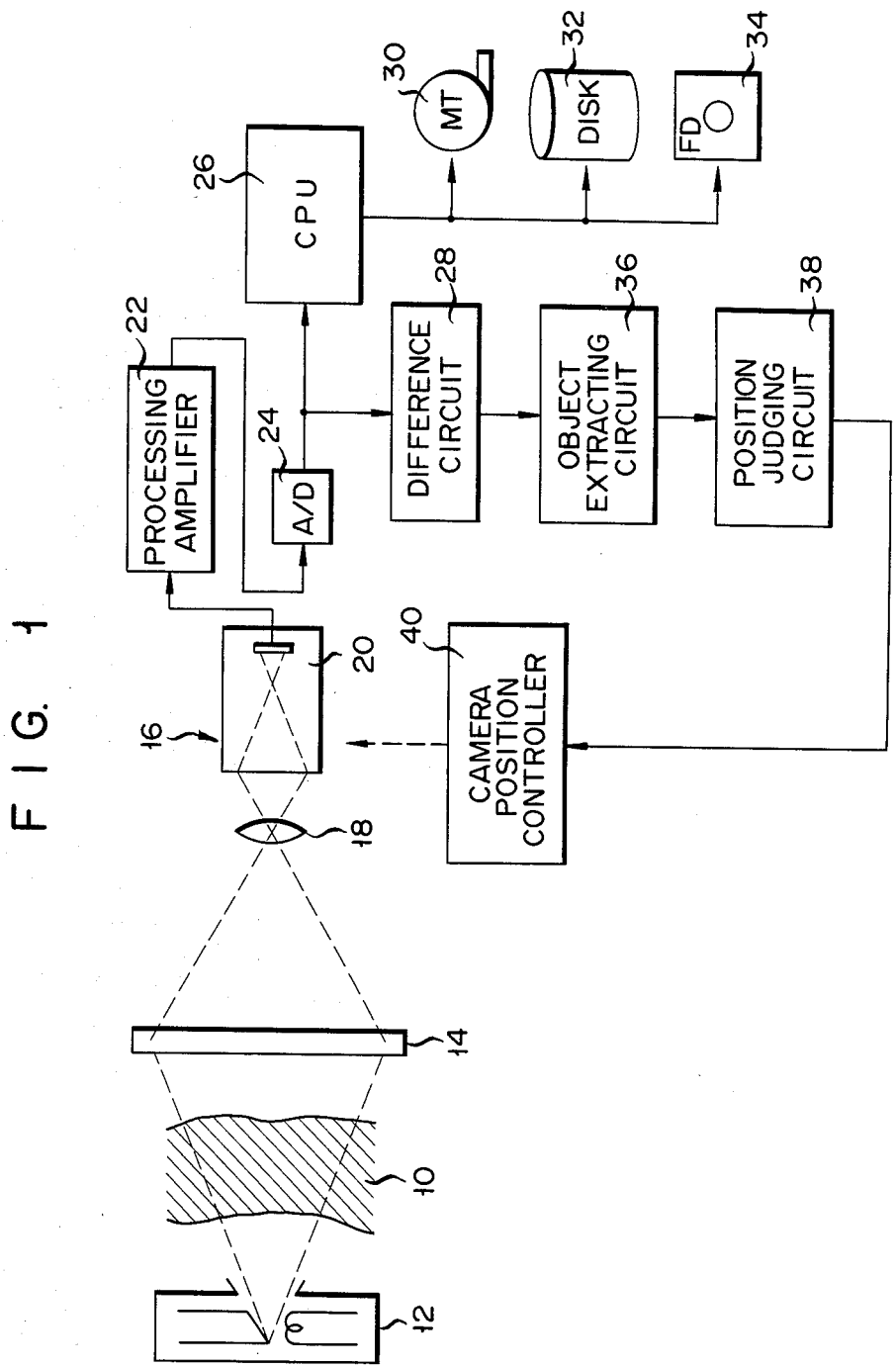
FIG. 1 is a block circuit diagram of an image input device according to an embodiment of the present invention.

An image input device according to an embodiment of the invention may now be described with reference to the accompanying drawings. FIG. 1 is a block diagram of this embodiment. An X-ray tube 12 and a fluorescent plate 14 are provided with a patient 10 therebetween. The fluorescent X-ray image obtained by the fluorescent plate 14 is imaged by a TV camera 16. The fluorescent plate 14 may be replaced by an image intensifier tube. The TV camera 16 is comprised of an objective lens 18 and an image pickup tube 20. While the X-ray tube 12 and fluorescent plate 14 are fixedly disposed, the TV camera 16 is made movable in three directions of X, Y and Z. Note here that the two directions defining the plane of the fluorescent plate 14 are represented by X and Y; and the direction intersecting the fluorescent plate 14 at right angles is represented by Z. The output signal from the image pickup tube 20 is input to a processing amplifier 22. The output signal from the processing amplifier 22 is supplied to a CPU 26 and a difference circuit 28 through an analog-to-digital converter 24. In the CPU 26, various image processings such as edge intensifying, etc., are performed with respect to the X-ray image. The image thus processed is stored to an external storage device including a magnetic tape 30, magnetic disk 32, floppy disk 34, etc. The difference circuit 28 determines the difference in brightness between the two X-ray pictures obtained at a prescribed time interval. More specifically, the difference circuit 28 is comprised of two frame memories and a subtracter. The output signal from the difference circuit 28 is supplied to an object extracting circuit 36. The signal of the object image extracted by the object extracting circuit 36 is supplied to a position judging circuit 38, in which it is judged whether or not the object image is located within a predetermined portion of a picture screen. The output judgement signal from the position judging circuit 38 is supplied to a camera position controller 40. Thus, the camera position is varied or changed in accordance with the output judgement signal. The camera position controller 40 has a mechanism for moving the TV camera 16 in the three directions, i.e., in the X, Y and Z directions.

Figure 2:
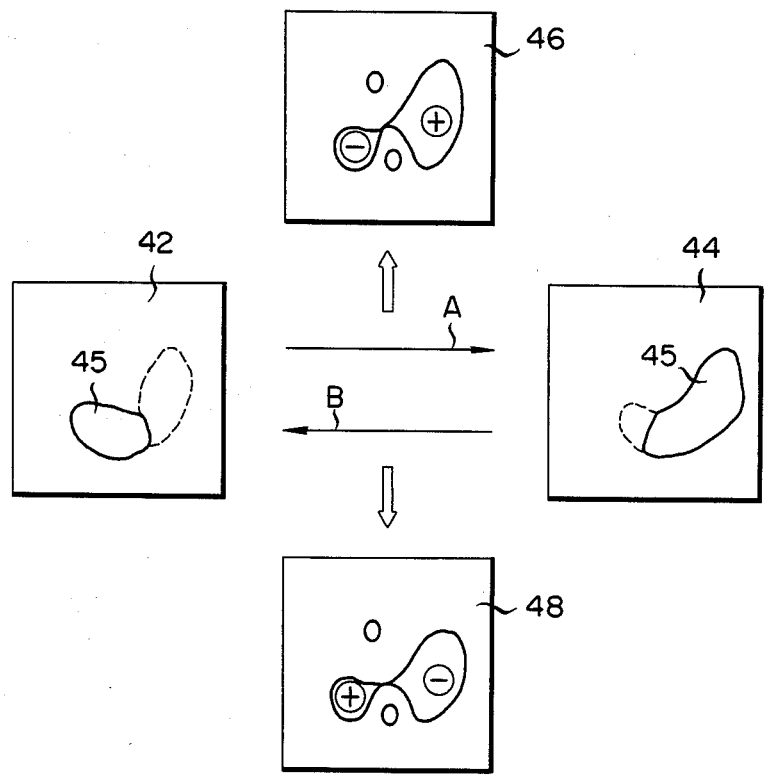
FIG. 2 is a view showing the operation of a difference circuit of FIG. 1.

The operation of this embodiment may be described as follows. Before imaging, a contrast medium is injected to the patient 10. X-rays are irradiated onto that portion of the patient 10 which is to undergo diagnosis. The fluorescent X-ray image produced by the fluorescent plate 14 is imaged by the TV camera 16. When it is found that the contrast of the object to be diagnosed is weak, a contrast medium is further injected to the patient 10. The output signal from the TV camera 16 is video-processed by the processing amplifier 22, thereby obtaining an image signal of the object in question. This image signal is converted to a digital signal by the analog-to-digital converter 24, which digital signal is input into the CPU 26, wherein various image processings are performed on an on-line basis. The image thus processed is stored in the external storage device. When image inputting is carried out, the position of the TV camera 16 is first manually adjusted so that the object image may be located at the central portion of the picture screen. Where the object image is still, or where the variation in configuration and position of the object image, if any, occurs within a small range, the camera position may be fixed. However, where the variation of the object image is wide or large, then the camera position is adjusted as follows so that the object image may be located at all times at the central portion of the picture screen. The TV camera 16 is of a motion picture type in which 30 frames are picked up per second. In the difference circuit 28, two picture signals obtained at a prescribed time interval among the output picture signals from the TV camera 16 are sampled. These two pictures may be two consecutive pictures, since these pictures are spaced from each other at a time interval corresponding to one frame. Preferably, however, they are more spaced from each other, for example, at a time interval corresponding to several frames. One of the sampled picture signals is subtracted from the other, thereby determining a difference therebetween. This difference corresponds to the movement or variation of the object. The state wherein the object is moved or varied is shown in FIG. 2. Assume now that a picture 44 is obtained in a prescribed period of time after a picture 42 is obtained. An object image 45 is enlarged or moves from a state indicated by picture 42 to a state indicated by picture 44 (i.e. . . . , in the direction indicated by arrow A). In the difference circuit 28, picture 42 is subtracted from picture 44, thereby obtaining a difference picture 46. Usually, the object image portion in the whole picture screen is made whitish (bright), while the remaining portion thereof is made blackish (dark). The difference between the two pictures is obtained as the difference in brightness between the picture cells of one picture and the corresponding picture cells of the other. The difference picture consists of three regions, i.e., the ⊕, ⊖ and 0 regions. Concerning the ⊕ region, the corresponding object image exists in picture 44, but not in picture 42. Regarding the ⊖ region, the corresponding object image exists in picture 42, but not in picture 44. As regards the 0 region, the corresponding object image exists or does not exist in picture 44 and in picture 42. Where the pictures 42 and 44 are picked-up in an order reversed from that mentioned above, i.e., the object image contracts or moves from the state indicated by picture 44 to the state indicated by picture 42 (in a direction indicated by arrow B), a difference picture 48 which has its ⊕ and ⊖ regions reversed from those of the difference picture 46 is obtained.

The object extracting circuit 36 extracts a zone covered by the ⊕ and ⊖ regions. The zone covered by these regions is a picture zone wherein any image variation occurs, i.e., an object image zone.

Figure 3A:
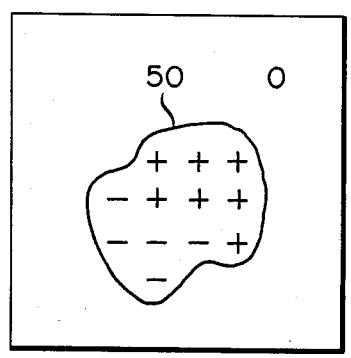
FIGS. 3A and 3B constitute a view for use in explaining the principle of "position judgement"
Figure 3B:
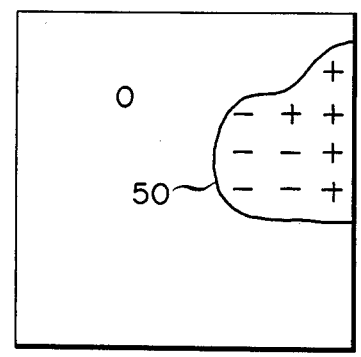
Figure 4A:
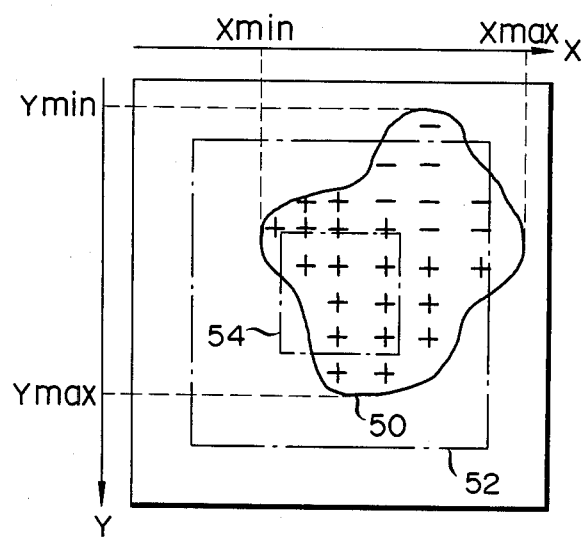
FIGS. 4A and 4B show actual examples of "position judgement".
Figure 4B:
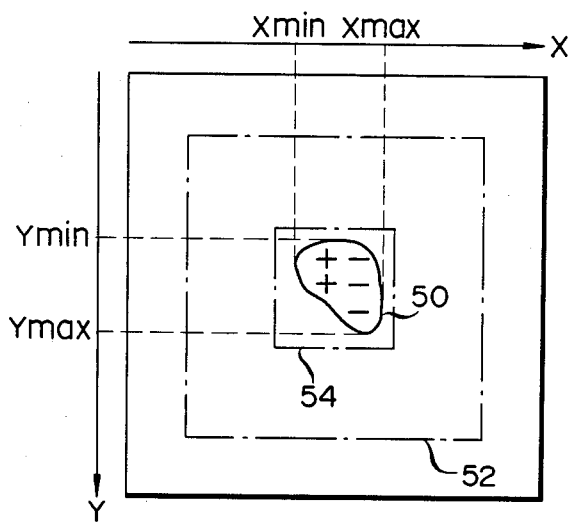

The position judging circuit 38 judges the position of the extracted zone in the picture screen. Where the extracted zone 50 covered by the ⊕ and ⊖ regions is located at the central portion of the picture screen, as shown in FIG. 3A, the object image sufficiently falls within the area of the picture screen. Where the extracted zone 50 is cut off by the side edge of the picture screen as shown in FIG. 3B, the object image is displaced from the central portion of the picture screen, namely is partly lost from the picture screen. More specifically, the maximum value Xmax and minimum value Xmin of the extracted zone 50 in the X direction, and the maximum value Ymax and the minimum value Ymin thereof in the Y direction, are determined respectively, whereby the position of the object image in question is judged as to whether or not it is located within a specified area of the picture screen. Image inputting is effected on an on-line basis. This specified area, therefore, is defined between an outer boundary 52, with somewhat smaller than the picture screen to provide some allowance for arrangement of the object image and an inner boundary 54 for determining the minimal magnification of the object image. If either the maximum value Xmax or the minimum value Xmin, or, if either the maximum value Ymax or the minimum value Ymin, is located outside of the outer boundary 52, as shown in FIG. 4A, the position judging circuit 38 will supply an output judgement signal to the camera position controller 40, to move the TV camera 16 in the X and Y directions. Thus, the composition of the picture will be so changed that the extracted image zone 50 may fall inside of the outer boundary 52. If all of the detected values Xmax, Xmin, Ymax, Ymin are located inside of the inner boundary 54 as shown in FIG. 4B, the size of the extracted image zone 50 in the picture screen is very small. Therefore, the magnification of the image in question is required to be increased. The increasing of the magnification of the image in question is achieved merely by moving the TV camera 16 in the Z direction to the fluorescent plate 14. Conversely, if the magnification of the object image is so large that all the detected values Xmax, Ymin, Ymax, Xmin are located outside of the outer boundary 52, the TV camera 16 will be moved in the Z direction away from the fluorescent plate 14. Thus, the object image, between the outer boundary 52 and inner boundary 54, is inputted into the CPU 26.

As has been described above, according to the present invention, where the position and configuration of the object vary, the composition of the object image can be changed accordingly. Consequently, it is possible to provide an image input device which enables the inputting of an image thereof, while the object image is being kept situated at the central portion of the picture screen, without any loss of the information or signals on the object image. If this image input device is applied to an X-ray image processing apparatus, the image processing can be effected on an on-line basis. This produces the effect of making it possible to shorten the time period required for X-ray imaging i.e., the time period required for a patient to be exposed to x-rays. The present invention is not limited to the above-mentioned embodiment, i.e., to a case wherein an image of the object is input through X-ray imaging. This invention can be applied to various modifications which composition is changed according to a difference picture between two pictures photographed.

What is claimed is:
1. An image input device comprising:
   imaging means for imaging a picture including an object image which is to undergo diagnosis, which object varies in position and configuration over time to define a variational portion in which the object image varies over time;
   object extracting means for extracting the variational portion within the object image by determining the difference in brightness between two pictures obtained by said imaging means;

position judging means for judging whether or not the object image variational portion extracted is located within a picture screen; and control means for controlling the imaging conditions of said imaging means, in accordance with the results of the judgment made by said position judging means such that the control means moves said imaging means in a direction parallel to the plane on which the object image is imaged, where the object image variational portion is partly or wholly lost from the picture screen.

2. An image input device according to claim 1, in which said imaging means comprises an x-ray source, a fluorescent plate for receiving the x-rays emitted from said x-ray source and passing through a human body which is to undergo diagnosis, and a television camera for imaging a fluorescent x-ray image produced by said fluorescent plate.

3. An image input device according to claim 1, in which said object extracting means extracts a zone wherein the difference in brightness between the two pictures obtained at a prescribed time interval is other than zero as the object image.

4. An image input device according to claim 1, in which said position judging means judges whether or not the object image variational portion falls within a specified range in the picture screen; and said control means moves said imaging means in a direction perpendicular to the plane on which the object image is imaged, where said object image variational portion has been judged as falling outside of said specified range.

5. An image input device according to claim 1, in which the output signal of said imaging means is processed on an on-line basis by an image processing means.

* * * * *